United States Patent
Komatsu et al.

(10) Patent No.: US 12,139,445 B2
(45) Date of Patent: Nov. 12, 2024

(54) METHOD OF PRODUCING HYDROFLUOROOLEFIN

(71) Applicant: AGC Inc., Tokyo (JP)

(72) Inventors: Takayuki Komatsu, Meguro-ku (JP); Tomoaki Takayama, Meguro-ku (JP); Satoshi Ariyama, Meguro-ku (JP); Taku Yamada, Chiyoda-ku (JP)

(73) Assignee: AGC Inc., Tokyo (JP)

( * ) Notice: Subject to any disclaimer, the term of this patent is extended or adjusted under 35 U.S.C. 154(b) by 443 days.

(21) Appl. No.: 17/652,954

(22) Filed: Mar. 1, 2022

(65) Prior Publication Data
US 2022/0267236 A1 Aug. 25, 2022

Related U.S. Application Data

(63) Continuation of application No. PCT/JP2020/032710, filed on Aug. 28, 2020.

(30) Foreign Application Priority Data
Sep. 6, 2019 (JP) ................................. 2019-163339

(51) Int. Cl.
| | | |
|---|---|---|
| C07C 17/23 | (2006.01) | |
| B01J 21/08 | (2006.01) | |
| B01J 23/62 | (2006.01) | |
| B01J 23/644 | (2006.01) | |

(52) U.S. Cl.
CPC .............. *C07C 17/23* (2013.01); *B01J 21/08* (2013.01); *B01J 23/62* (2013.01); *B01J 23/626* (2013.01); *B01J 23/628* (2013.01); *B01J 23/6447* (2013.01)

(58) Field of Classification Search
CPC .......... C07C 17/23; C07C 21/18; B01J 23/62; B01J 23/626; B01J 23/628; B01J 23/6447; B01J 21/08
See application file for complete search history.

(56) References Cited

U.S. PATENT DOCUMENTS

| | | |
|---|---|---|
| 2012/0123173 A1 | 5/2012 | Hibino et al. |
| 2012/0302804 A1 | 11/2012 | Sakyu et al. |
| 2017/0158587 A1 | 6/2017 | Terazono et al. |
| 2018/0251414 A1 | 9/2018 | Terazono et al. |

FOREIGN PATENT DOCUMENTS

| | | |
|---|---|---|
| CN | 102471192 A | 5/2012 |
| CN | 102762523 A | 10/2012 |
| WO | WO 2016/031777 A1 | 3/2016 |

OTHER PUBLICATIONS

International Search Report issued Nov. 2, 2020 in PCT/JP2020/032710 filed on Aug. 28, 2020, citing documents AA-AB & AO therein, 2 pages.

*Primary Examiner* — Jafar F Parsa
(74) *Attorney, Agent, or Firm* — Oblon, McClelland, Maier & Neustadt, L.L.P.

(57) ABSTRACT

A method of producing a hydrofluoroolefin includes reacting a chlorofluoroolefin that is represented by Formula (I) or Formula (II) and that has 8 or less carbon atoms with a hydrogen molecule, in the presence of an intermetallic compound containing at least one first metal that is selected from the group consisting of palladium, platinum, rhodium, copper and iridium, and containing a second metal that is different from the first metal, to obtain a hydrofluoroolefin in which a hydrogen atom is substituted for at least a chlorine atom represented by Cl among chlorine atoms contained in Formula (I) or Formula (II).

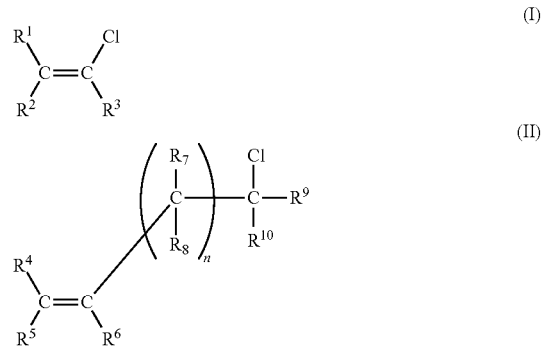

11 Claims, No Drawings

METHOD OF PRODUCING HYDROFLUOROOLEFIN

CROSS-REFERENCE TO RELATED APPLICATIONS

This application is a Continuation Application of International Application No. PCT/JP2020/032710, filed Aug. 28, 2020, the disclosure of which is incorporated herein by reference in its entirety. Further, this application claims priority from Japanese Patent Application No. 2019-163339, filed Sep. 6, 2019, the disclosure of which is incorporated herein by reference in its entirety.

TECHNICAL FIELD

The present invention relates to a method of producing a hydrofluoroolefin.

BACKGROUND ART

Hydrofluorocarbons obtained by substituting a hydrogen atom for a chlorine atom contained in chlorofluorocarbon are useful as substitute compounds for chlorofluorocarbons used as refrigerants or solvents.

In particular, it is known that hydrofluoroolefin, which is a kind of hydrofluorocarbon, contains a carbon-carbon double bond in its molecule and is easily decomposed by ultraviolet rays and has a low global warming potential. Therefore, there is a demand for a method of efficiently producing a hydrofluoroolefin from a chlorofluoroolefin, which is a kind of chlorofluorocarbon, while maintaining a carbon-carbon double bond.

As a method of producing a hydrofluoroolefin from a chlorofluoroolefin, a method of reacting a specific chlorofluoroolefin with hydrogen in the presence of a catalyst supported on a carrier to obtain a specific hydrofluoroolefin is known (for example, refer to Patent Document 1). In Patent Document 1, a catalyst made of an alloy that includes at least one platinum group element selected from the group consisting of palladium and platinum, and at least one second element selected from the group consisting of manganese, copper, aluminum, gold, lithium, sodium, potassium, magnesium, silver, zinc, cadmium, indium, silicon, germanium, tin, lead, arsenic, antimony and bismuth, is used.

PRIOR ART DOCUMENTS

Patent Documents

Patent Document 1: International Publication Number WO 2016/031777

SUMMARY OF INVENTION

Technical Problem

According to the method described in Patent Document 1, in the production of hydrofluoroolefins from chlorofluoroolefins, the residual ratio of a carbon-carbon double bond and the selectivity of a substitution reaction of a hydrogen atom for a chlorine atom can be improved. However, the reduction of by-products is not sufficient from the viewpoint of improving productivity, and a metal catalyst capable of further improving selectivity is required.

The present disclosure has been made in view of the above-mentioned conventional circumstances, and the present disclosure aims to provide a method of producing a hydrofluoroolefin in which the residual ratio of a carbon-carbon double bond and the selectivity of a substitution reaction of a hydrogen atom for a chlorine atom are excellent when producing hydrofluoroolefins from chlorofluoroolefins.

Solution to Problem

Specific means for achieving the above-described object are as follows.

<1> A method of producing a hydrofluoroolefin, comprising:
reacting a chlorofluoroolefin that is represented by following Formula (I) or following Formula (II) and that has 8 or less carbon atoms with a hydrogen molecule, in the presence of an intermetallic compound containing at least one first metal that is selected from the group consisting of palladium, platinum, rhodium, copper and iridium, and containing a second metal that is different from the first metal, to obtain a hydrofluoroolefin in which a hydrogen atom is substituted for at least a chlorine atom represented by Cl among chlorine atoms contained in Formula (I) or Formula (II):

wherein, in Formula (I), each of $R^1$ to $R^3$ independently represents a hydrogen atom, a fluorine atom, a chlorine atom or an alkyl group that may be substituted with a fluorine atom or a chlorine atom, and at least one fluorine atom is included in Formula (I);

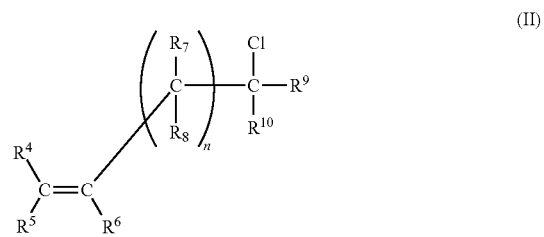

wherein, in Formula (II), each of $R^4$ to $R^{10}$ independently represents a hydrogen atom, a fluorine atom, a chlorine atom or an alkyl group that may be substituted with a fluorine atom or a chlorine atom, at least one fluorine atom is included in Formula (II), and n is an integer from 0 to 5.

<2> The method of producing a hydrofluoroolefin according to <1>, wherein a molar ratio of the first metal to the second metal which are contained in the intermetallic compound, first metal/second metal, is from 1 to 5.

<3> The method of producing a hydrofluoroolefin according to <2>, wherein the molar ratio of the first metal to the second metal which are contained in the intermetallic compound, first metal/second metal, is from 2 to 4.

<4> The method of producing a hydrofluoroolefin according to <1>, wherein the intermetallic compound is at least one selected from the group consisting of $Pd_3Bi$, $Pd_3In$, $Pd_3Sn$ and $Pd_3Pb$.

<5> The method of producing a hydrofluoroolefin according to any one of <1> to <4>, wherein the chlorofluoroolefin is a compound represented by following Formula (III):

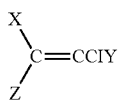

(III)

wherein, in Formula (III), X represents a fluorine atom or a chlorine atom, Y represents a hydrogen atom, a fluorine atom or a chlorine atom, and Z represents a fluorine atom or a methyl group that may be substituted with a fluorine atom.

<6> The method of producing a hydrofluoroolefin according to <5>, wherein the compound represented by Formula (III) includes 1,1-dichloro-2,3,3,3-tetrafluoropropene or 1-chloro-2,3,3,3-tetrafluoropropene.

<7> The method of producing a hydrofluoroolefin according to any one of <1> to <6>, wherein the intermetallic compound is supported on a carrier.

<8> The method of producing a hydrofluoroolefin according to <7>, wherein the carrier includes at least one of a carbon material or an oxide material.

<9> The method of producing a hydrofluoroolefin according to <7> or <8>, wherein an amount of the intermetallic compound that is supported is from 0.1% by mass to 10% by mass with respect to the carrier.

<10> The method of producing a hydrofluoroolefin according to any one of <7> to <9>, wherein the chlorofluoroolefin and the hydrogen molecule are introduced into a catalyst layer that is filled with the carrier supporting the intermetallic compound and are reacted in a gas phase.

<11> The method of producing a hydrofluoroolefin according to any one of <7> to <9>, wherein the chlorofluoroolefin and the hydrogen molecule are reacted in a liquid phase in the presence of the carrier that is supporting the intermetallic compound.

Advantageous Effects of Invention

According to the present disclosure, a method of producing a hydrofluoroolefin in which the residual ratio of a carbon-carbon double bond and the selectivity of a substitution reaction of a hydrogen atom for a chlorine atom are excellent when producing hydrofluoroolefins from chlorofluoroolefins is provided.

DESCRIPTION OF EMBODIMENTS

Embodiments of the disclosure are described below in detail. It is noted here, however, that the disclosure is not restricted to the below-described embodiments. In the below-described embodiments, the constituents thereof (including element steps and the like) are not indispensable unless otherwise specified. The same applies to the numerical values and ranges thereof, without restricting the disclosure.

In the disclosure, those numerical ranges that are expressed with "to" each denote a range that includes the numerical values stated before and after "to" as the minimum value and the maximum value, respectively.

In a set of numerical ranges that are stated stepwise in the disclosure, the upper limit value or the lower limit value of a numerical range may be replaced with the upper limit value or the lower limit value of other numerical range. Further, in a numerical range stated in the disclosure, the upper limit or the lower limit of the numerical range may be replaced with a relevant value indicated in any of Examples.

[Method of Producing Hydrofluoroolefin]

The method of producing a hydrofluoroolefin of the present disclosure (hereinafter may be referred to as a specific hydrofluoroolefin) is a method of reacting a chlorofluoroolefin that is represented by above-described Formula (I) or above-described Formula (II) and that has 8 or less carbon atoms (hereinafter may be referred to as a specific chlorofluoroolefin) with a hydrogen molecule (hereinafter may simply be referred to as "hydrogen"), in the presence of an intermetallic compound containing at least one first metal that is selected from the group consisting of palladium, platinum, rhodium, copper and iridium, and containing a second metal that is different from the first metal (hereinafter may be referred to as a specific intermetallic compound), to obtain a hydrofluoroolefin in which a hydrogen atom is substituted for at least a chlorine atom represented by Cl among chlorine atoms contained in above-described Formula (I) or above-described Formula (II).

According to the method of producing a hydrofluoroolefin of the present disclosure, in the production of a hydrofluoroolefin from a chlorofluoroolefin, the residual ratio of a carbon-carbon double bond and the selectivity of the substitution reaction of a hydrogen atom for a chlorine atom are excellent.

Alloy catalysts, which are known as metal catalysts, have flexible chemical formulas in terms of the ratio of a first metal to a second metal and are composed of various metal elements, and it is easy to select desirable metal combinations and metal compounding ratios. On the other hand, the mixed state of metal atoms tends to be irregular, and it may be difficult to industrially obtain an optimal catalyst structure. In a case in which an alloy catalyst is composed of a first metal (A) and a second metal (B), the alloy catalyst is represented by $AB_x$ (x being variable within a predetermined range).

On the other hand, an intermetallic compound used as a catalyst in the present disclosure includes at least one first metal selected from the group consisting of palladium, platinum, rhodium, copper and iridium, and a second metal that is different from the first metal. An intermetallic compound is a compound formed by bonding two or more metal elements at a simple integer ratio. In a case in which an intermetallic compound is composed of a first metal (A) and a second metal (B), the intermetallic compound is represented by $A_nB_m$ (n and m being integers).

Intermetallic compounds, whose constituent metals are regularly arranged at the atomic level, differ from bimetallic catalysts in which the same metal elements are segregated to form island structures or ordinary alloy catalysts in which two metal elements are randomly mixed. For that reason, it is considered that the first metal such as palladium is uniformly affected by the second metal, and the residual ratio of a carbon-carbon double bond and the selectivity of the substitution reaction of a hydrogen atom for a chlorine atom can be improved.

Hereinafter, a specific intermetallic compound and a specific chlorofluoroolefin used in the method of producing a hydrofluoroolefin of the present disclosure, a specific hydrofluoroolefin, which is the reaction product, the reaction conditions and the like will be described in detail.

<Specific Intermetallic Compound>

The intermetallic compound used in the present disclosure is not particularly limited as long as it includes at least one first metal selected from the group consisting of palladium, platinum, rhodium, copper and iridium, and a second metal that is different from the first metal.

As the first metal contained in the specific intermetallic compound, palladium, platinum, rhodium and iridium are preferable, and palladium is more preferable.

The second metal contained in the specific intermetallic compound is a metal that is different from the first metal, and a metal capable of forming an intermetallic compound with the first metal is appropriately selected. Examples of the second metal include metals of group 6, group 7, group 8, group 11, group 12, group 13, group 14, and group 15. Specific examples thereof include bismuth, indium, tin, lead, iron, gallium, germanium, zinc, and antimony.

From among the above-mentioned second metals, at least one selected from the group consisting of tin, bismuth, lead and indium is preferable from the viewpoint of reducing excessive hydrogen reduction activity of the first metal and and enabling synthesis of the target hydrofluoroolefin with high selectivity.

In the substitution reaction of the specific chlorofluoroolefin by a hydrogen atom, not only the substitution reaction of a hydrogen atom for a chlorine atom, but also the hydrogenation reaction to a carbon-carbon double bond proceeds. In the present disclosure, the hydrogenation reaction to a carbon-carbon double bond caused by excessive hydrogen reduction activity of the first metal, and the substitution reaction of a hydrogen atom for a fluorine atom, are defined as an over-reduction reaction, and the product of the over-reduction reaction is referred to as an over-reduced product.

The specific intermetallic compound may be a binary compound, that is, an intermetallic compound containing two metals, or may be a ternary or higher multi-element intermetallic compound. In a case in which the specific intermetallic compound is a ternary or higher multi-element intermetallic compound, two or more metal elements may be included as the first metal, and two or more metal elements may be included as the second metal.

The specific intermetallic compound is preferably a binary compound containing one first metal and one second metal.

The molar ratio of the first metal to the second metal which are contained in the specific intermetallic compound, first metal/second metal, is not particularly limited as long as it is a ratio at which an intermetallic compound can be formed by the first metal and the second metal, with a ratio of 1 to 5 being preferable, a ratio of 2 to 4 being more preferable, and a ratio of 3 being even more preferable.

The specific intermetallic compound may contain defects such as voids, gaps, anti site defects, and substitutions with impurity atoms. Further, all of the first metal and the second metal which are contained in the specific intermetallic compound may form an intermetallic compound, and a part of the first metal and the second metal may indicate a metallographic structure other than an intermetallic compound, such as a solid solution.

In a case in which both an intermetallic compound and the metallographic structure other than an intermetallic compound, such as a solid solution, coexist, when the peak with the strongest diffraction intensity among the diffraction peaks obtained by structural analysis by X-ray diffractometry for the substance indicates an intermetallic compound, the substance is considered to be an intermetallic compound.

Whether or not the metal component used as a catalyst is an intermetallic compound can be confirmed by X-ray diffractometry (XRD). By identifying the plane indices of the XRD diffraction peaks, the structure of the metal component can be identified.

For example, the diffraction peaks can be measured by using a fully automatic multipurpose X-ray diffractometer (SmartLab) from Rigaku Corporation. The analysis conditions and X-ray source are as follows.

Measurement range (2θ): 20 deg to 60 deg
Scanning speed: 0.3 deg/min
X-ray source: CuKα radiation (wavelength: 1.54 Å)

The types of metal elements contained in the intermetallic compound and the ratio thereof are, for example, determined using means such as an inductivity coupled plasma optical emission spectrometer (ICP-OES) or an X-ray fluorescence (XRF) analyzer.

Specific examples of the specific intermetallic compound include $Pd_3Bi$, $Pd_3In$, $Pd_3Sn$, $Pd_3Pb$, $PtBi$, $Pt_3In$, $Pt_3Sn$, $Pt_3Pb$, $RhBi$, $RhIn$, $Rh_2Sn$, $RhPb$, $IrBi$ and $Cu_3Sn$. Among these, at least one selected from the group consisting of $Pd_3Bi$, $Pd_3In$, $Pd_3Sn$ and $Pd_3Pb$ is preferable, and $Pd_3Bi$ is more preferable.

The specific intermetallic compound may be supported on a carrier or may be in a state of not being supported. It is preferable to use a carrier because the specific intermetallic compound can be easily dispersed by using a carrier. In the present disclosure, a carrier on which a catalyst such as a specific intermetallic compound is supported may be referred to as a catalyst-supporting carrier.

In a case in which the specific intermetallic compound is supported on a carrier, examples of the carrier include at least one of a carbon material such as activated carbon, carbon black, and carbon fiber, and oxide materials such as alumina, silica, titania, zirconia, alkali metal oxides and alkaline earth metal oxides, and it is preferable to include at least one selected from the group consisting of activated carbon, carbon black, carbon fiber, alumina, silica, titania and zirconia. Among these, activated carbon, alumina, silica, and zirconia are more preferable because they have a large specific surface area and easily support a catalyst, and activated carbon is more preferable from the viewpoint that by-production of an over-reduced product can be better suppressed.

Examples of the activated carbon include activated carbon prepared from wood, charcoal, fruit husks such as coconut husks, peat, lignite and coal. Examples of the form of activated carbon include an aggregate of briquette having a length of about 2 mm to 7 mm, pulverized coal of about 4 mesh to 50 mesh, and granular charcoal. Among these, an aggregate of briquette or pulverized coal of 4 mesh to 30 mesh is preferable.

Examples of alumina include alumina having different crystalline states such as α-alumina, γ-alumina, and θ-alumina. The crystalline state is not particularly limited, and alumina can be widely used from γ-alumina having a large specific surface area to α-alumina having high crystallinity and a small specific surface area. Although the shape of the alumina is not necessarily limited, the alumina is preferably formed in a spherical shape or a pellet shape because the filling property when filling a reactor, the flowability of the reaction gas and the like are favorable.

Examples of zirconia include various crystal forms having different crystalline states such as monoclinic crystals, tetragonal crystals, cubic crystals, and metastable tetragonal crystals, and amorphous zirconium hydroxide, and the crystalline state is not particularly limited and any zirconia can be widely used. Although the shape of the zirconia is not necessarily limited, the zirconia is preferably formed in a spherical shape or a pellet shape because the filling property when filling the reactor, the flowability of the reaction gas and the like are favorable.

The amount of the intermetallic compound that is supported with respect to the carrier is preferably 0.1% by mass to 10% by mass, and more preferably 0.5% by mass to 6% by mass. If the supported amount is 0.1% by mass or more, the conversion rate of the specific chlorofluoroolefin and hydrogen tends to improve. On the other hand, if the supported amount is 10% by mass or less, excessive temperature rise of the catalyst layer due to reaction heat tends to be suppressed, and by-production of an over-reduced product tends to be easily suppressed.

The specific surface area of the carrier is preferably 10 m$^2$/g to 2000 m$^2$/g, and more preferably 100 m$^2$/g to 1500 m$^2$/g. If the specific surface area of the carrier is 10 m$^2$/g or more, the conversion rate of the specific chlorofluoroolefin and hydrogen is further improved, while if the specific surface area of the carrier is 2000 m$^2$/g or less, it becomes easier to suppress by-production of an over-reduced product.

The method of producing the catalyst-supporting carrier is not particularly limited, and the catalyst-supporting carrier can be produced by a known method. The catalyst-supporting carrier is preferably produced by a co-impregnation method or a successive impregnation method.

In the co-impregnation method, a metal salt mixed solution containing a metal salt of the first metal and a metal salt of the second metal is brought into contact with a carrier, and the metal salt of the first metal and the metal salt of the second metal are adsorbed on the surface of the carrier, and after drying the impregnated carrier, the carrier is heat-treated in an atmosphere of hydrogen and a specific intermetallic compound containing the first metal and the second metal is supported on the surface of the carrier.

In the successive impregnation method, a metal salt solution containing a metal salt of the first metal is brought into contact with a carrier, the metal salt of the first metal is adsorbed on the surface of the carrier, and after the impregnated carrier is dried, the carrier is heat-treated in an atmosphere of hydrogen and the first metal is supported on the carrier. Next, a metal salt solution containing the metal salt of the second metal is brought into contact with the carrier, the metal salt of the second metal is adsorbed on the surface of the carrier, and after the impregnated carrier is dried, the carrier is heat-treated in an atmosphere of hydrogen and the specific intermetallic compound containing the first metal and the second metal is supported on the surface of the carrier. In the successive impregnation method, after the metal salt of the second metal is supported on the carrier, the metal salt of the first metal may be supported on the carrier, and then the heat treatment may be performed.

In the co-impregnation method or the successive impregnation method, the heating temperature for supporting the specific intermetallic compound on the surface of the carrier is preferably higher than 700° C., and more preferably 750°

C. or higher. If the heating temperature is 700° C. or lower, an intermetallic compound is less likely to be formed.

In a case in which a specific intermetallic compound that is not supported on a carrier is used as a catalyst, the method of producing the specific intermetallic compound is not particularly limited, and the specific intermetallic compound may be produced by an arc melting method or the like. The melting method is a method of producing an intermetallic compound by melting an amount of the first metal and the second metal which is suitable for forming an intermetallic compound. In the mixture of metal elements to be subjected to the melting method, the first metal and the second metal are present at a molar ratio corresponding to the molar ratio of the metal elements in the intermetallic compound. Melting of the metals can be performed in an atmosphere of an inert gas such as argon or nitrogen. The obtained intermetallic compound can be crushed as necessary such that a desired particle size can be obtained. The crushing method is not particularly limited, and the crushing can be performed using a ball mill, a swing mill, a planetary mill or the like in an inert atmosphere such as argon.

<Specific Chlorofluoroolefin and Specific Hydrofluoroolefin>

The method of producing a hydrofluoroolefin of the present disclosure is a method of producing a specific hydrofluoroolefin by reacting a specific chlorofluoroolefin with a hydrogen molecule.

Hereinafter, the specific chlorofluoroolefin as a raw material and the specific hydrofluoroolefin as a reaction product will be described.

The specific hydrofluoroolefin which is a reaction product may or may not contain a chlorine atom. However, the number of chlorine atoms contained in the specific hydrofluoroolefin is less than the number of chlorine atoms contained in the specific chlorofluoroolefin.

The chlorofluoroolefin represented by the following Formula (I) contains one carbon-carbon double bond in the molecule. The chlorofluoroolefin represented by the general Formula (I) is preferably an α-olefin. That is, each of R$^1$, R$^2$, and R$^3$ is a hydrogen atom, a fluorine atom, or a chlorine atom, or it is preferable that any one of R$^1$, R$^2$ or R$^3$ is an alkyl group that may be substituted with a fluorine atom or a chlorine atom, and each of the others is a hydrogen atom, a fluorine atom or a chlorine atom. The carbon number of the chlorofluoroolefin represented by the following general Formula (I) is preferably 7 or less, and more preferably 6 or less.

(I)

In Formula (I), each of R$^1$ to R$^3$ independently represents a hydrogen atom, a fluorine atom, a chlorine atom or an alkyl group that may be substituted with a fluorine atom or a chlorine atom, and at least one fluorine atom is included in the Formula (I).

In Formula (I), the carbon number of the alkyl group represented by R$^1$ to R$^3$ is preferably 6 or less, more preferably 5 or less, and still more preferably 4 or less.

Specific examples of the alkyl group represented by R$^1$ to R$^3$ include a methyl group, an ethyl group, an n-propyl group, an isopropyl group, an n-butyl group, an isobutyl group, a t-butyl group, an s-butyl group, an n-pentyl group and an n-hexyl group.

At least some of the hydrogen atoms configuring the alkyl group represented by $R^1$ to $R^3$ may be substituted with a fluorine atom or a chlorine atom. In the alkyl group represented by $R^1$ to $R^3$, the position of the hydrogen atom that is substituted with the fluorine atom or the chlorine atom is not particularly limited.

In a case in which the chlorofluoroolefin represented by Formula (I) is used as a raw material, according to the method of producing a hydrofluoroolefin of the present disclosure, a hydrofluoroolefin is produced in which a hydrogen atom is substituted for at least a chlorine atom represented by Cl among the chlorine atoms contained in Formula (I). In a case in which the chlorofluoroolefin represented by Formula (I) contains a chlorine atom other than the chlorine atom represented by Cl in Formula (I) (hereinafter may be referred to as another chlorine atom), a hydrofluoroolefin in which a hydrogen atom is substituted for only the chlorine atom represented by Cl among the chlorine atoms contained in Formula (I) may be produced, and a hydrofluoroolefin in which a hydrogen atom is substituted for the chlorine atom represented by Cl among the chlorine atoms contained in Formula (I) and the other chlorine atom may be produced.

The chlorofluoroolefin represented by the following Formula (II) contains one carbon-carbon double bond in the molecule. The chlorofluoroolefin represented by the general Formula (I) is preferably an α-olefin. That is, it is preferable that each of $R^4$, $R^5$, and $R^6$ is a hydrogen atom, a fluorine atom, or a chlorine atom. The carbon number of the chlorofluoroolefin represented by the following general Formula (II) is preferably 7 or less, and more preferably 6 or less.

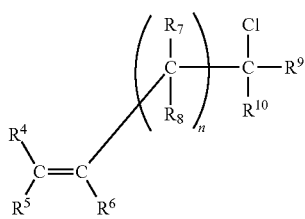

In Formula (II), each of $R^4$ to $R^{10}$ independently represents a hydrogen atom, a fluorine atom, a chlorine atom or an alkyl group that may be substituted with a fluorine atom or a chlorine atom, at least one fluorine atom is included in Formula (II), and n represents an integer from 0 to 5.

In Formula (II), specific examples of the alkyl group represented by $R^4$ to $R^{10}$ include the same as those in a case of the alkyl group represented by $R^1$ to $R^3$ in Formula (I). However, in Formula (II), the carbon number of the alkyl group represented by $R^4$ to $R^{10}$ is preferably 5 or less, more preferably 4 or less, and even more preferably 3 or less.

In a case in which the chlorofluoroolefin represented by Formula (II) is used as a raw material, according to the method of producing a hydrofluoroolefin of the present disclosure, a hydrofluoroolefin is produced in which a hydrogen atom is substituted for at least the chlorine atom represented by Cl among the chlorine atoms contained in Formula (II). In a case in which the chlorofluoroolefin represented by Formula (II) contains another chlorine atom apart from the chlorine atom represented by Cl in Formula (II), a hydrofluoroolefin in which a hydrogen atom is substituted for only the chlorine atom represented by Cl among the chlorine atoms contained in Formula (II) may be produced, and a hydrofluoroolefin in which a hydrogen atom is substituted for the chlorine atom represented by Cl among the chlorine atoms contained in Formula (II) and the other chlorine atom may be produced.

The specific chlorofluoroolefin is preferably a compound represented by the following Formula (III).

In Formula (III), X represents a fluorine atom or a chlorine atom, Y represents a hydrogen atom, a fluorine atom or a chlorine atom, and Z represents a fluorine atom or a methyl group that may be substituted with a fluorine atom.

The specific hydrofluoroolefin produced from the specific chlorofluoroolefin represented by Formula (III) is a compound represented by the following Formula (IV).

In Formula (IV), in a case in which X in Formula (III) is a fluorine atom, X is a fluorine atom; in a case in which X in Formula (III) is a chlorine atom, X is a chlorine atom or a hydrogen atom; in a case in which Y in Formula (III) is a fluorine atom, Y' is a fluorine atom; in a case in which Y in Formula (III) is a chlorine atom, Y' is a chlorine atom or a hydrogen atom; in a case in which Y in the Formula (III) is a hydrogen atom, Y' is a hydrogen atom; and Z is the same as Z in Formula (III).

As the compound represented by Formula (III), from the viewpoint of a product having high cooling efficiency and expecting an alternative refrigerant that is environmentally friendly, chlorotrifluoroethylene, 1,2-dichloro-1,2-difluoroethylene, 1,2-dichloro-1,3,3,3-tetrafluoropropene ($CF_3CCl=CFCl$), 1,1,2-trichloro-3,3,3-trifluoropropene ($CF_3CCl=CCl_2$), 1,1-dichloro-2,3,3-trifluoropropene ($CHF_2CF=CCl_2$), 1,1-dichloro-2,3,3,3-tetrafluoropropene ($CF_3CF=CCl_2$) (hereinafter also referred to as "CFO-1214ya"), and 1-chloro-2,3,3,3-tetrafluoropropene ($CF_3CF=CHCl$) (hereinafter also referred to as "HCFO-1224yd") are preferable, and CFO-1214ya or HCFO-1224yd are more preferable. Further, a mixture of CFO-1214ya and HCFO-1224yd is preferable.

For example, in a case in which the specific chlorofluoroolefin of the raw material is chlorotrifluoroethylene, the trifluoroethylene obtained by the reaction represented by the following Formula (A) is contained in the reaction product as the specific hydrofluoroolefin.

$$CFCl=CF_2 + H_2 \rightarrow CHF=CF_2 + HCl \qquad (A)$$

In a case in which the specific chlorofluoroolefin of the raw material is 1,2-dichloro-1,2-difluoroethylene, the 1,2-difluoroethylene obtained by the reaction represented by the following Formula (B) is contained in the reaction product as the specific hydrofluoroolefin. Note that in a case in which the specific chlorofluoroolefin and the specific hydrofluoroolefin contain a cis-trans isomer (geometric isomer), the following chemical Formula does not indicate the distinction between the cis isomer and the trans isomer.

$$CFCl=CFCl+2H_2 \rightarrow CHF=CHF+2HCl \quad (B)$$

In a case in which the specific chlorofluoroolefin of the raw material is 1,2-dichloro-1,3,3,3-tetrafluoropropene, the 1,3,3,3-tetrafluoropropene obtained by the reaction represented by the following Formula (C) is contained in the reaction product as the specific hydrofluoroolefin.

$$CF_3CCl=CFCl+2H_2 \rightarrow CF_3CH=CHF+2HCl \quad (C)$$

In a case in which the specific chlorofluoroolefin of the raw material is 1,1,2-trichloro-3,3,3-trifluoropropene, the 1-chloro-3,3,3-trifluoropropene obtained by the reaction represented by the following Formula (D) is contained in the reaction product as the specific hydrofluoroolefin.

$$CF_3CCl=CCl_2+2H_2 \rightarrow CF_3CH=CHCl+2HCl \quad (D)$$

In a case in which the specific chlorofluoroolefin of the raw material is 1,1-dichloro-2,3,3-trifluoropropene, the 1-chloro-2,3,3-trifluoropropene obtained by the reaction represented by the following Formula (E) is contained in the reaction product as the specific hydrofluoroolefin.

$$CHF_2CF=CCl_2+H_2 \rightarrow CHF_2CF=CHCl+HCl \quad (E)$$

In a case in which the specific chlorofluoroolefin of the raw material is CFO-1214ya, HCFO-1224yd obtained by the reaction represented by the following Formula (F) is contained in the reaction product as the specific hydrofluoroolefin.

$$CF_3CF=CCl_2+H_2 \rightarrow CF_3CF=CHCl+HCl \quad (F)$$

In a case in which the specific chlorofluoroolefin of the raw material is HCFO-1224yd, the 2,3,3,3-tetrafluoro-1-propene (HFO-1234yf) obtained by the reaction represented by the following Formula (G) is contained in the reaction product as the specific hydrofluoroolefin.

$$CF_3CF=CHCl+H_2 \rightarrow CF_3CF=CH_2+HCl \quad (G)$$

Further, the hydrofluoroolefin produced by the method of producing a hydrofluoroolefin of the present disclosure may be a mixture of two or more hydrofluoroolefins having different substitution positions from a chlorine atom to a hydrogen atom. When the hydrofluoroolefin is a mixture, it may be a mixture of a target reaction product and an intermediate product.

The substitution reaction of a hydrogen atom for a chlorine atom may be carried out in a gas phase or in a liquid phase as long as the above-mentioned intermetallic compound is used.

Examples of the reaction method include the following method (α) or method (β), and method (α) is preferable.

Method (α): A method of reacting the specific chlorofluoroolefin with hydrogen in a gas phase, in the presence of an intermetallic compound.

Method (β): A method of reacting the specific chlorofluoroolefin with hydrogen in a liquid phase, in the presence of an intermetallic compound.

<Method (α)>

Examples of the method (α) include a method in which the specific chlorofluoroolefin and hydrogen are introduced into a reactor filled with a catalyst-supporting carrier and are reacted in a gas phase. A specific example of the method includes introducing a gas containing a specific chlorofluoroolefin gas and hydrogen gas (hereinafter also referred to as "raw material mixed gas") into the reactor and causing the reaction.

The catalyst layer is obtained by filling the reactor with the catalyst-supporting carrier described above. The filling density of the catalyst-supporting carrier is preferably 0.3 g/cm$^3$ to 1 g/cm$^3$, and more preferably 0.4 g/cm$^3$ to 0.8 g/cm$^3$. If the filling density is 0.3 g/cm$^3$ or higher, the filling amount of the catalyst-supporting carrier per unit volume is large, and productivity increases due to there being a large amount of gas to react. On the other hand, if the filling density is 1 g/cm$^3$ or lower, it is possible to prevent the temperature of the catalyst layer described below from rising too much, and it is easy to maintain the maximum temperature of the catalyst layer described below at a desired temperature or lower.

As the reactor, a typical flow-type reactor used in a gas-solid heterogeneous catalytic reaction, in which the catalyst-supporting carrier is a solid and in which the reaction fluid is a gas, can be used. Such flow-type reactors are broadly classified into fixed bed reactors and fluidized bed reactors. In fixed bed reactors, various molded bodies of the catalyst-supporting carrier are filled in order to reduce pressure loss of the reaction fluid. Further, a method in which a catalyst-supporting carrier is filled in the same manner as in a fixed bed reactor, moved by the gravity of the catalyst-supporting carrier, and the catalyst-supporting carrier is extracted from the bottom of the reactor and regenerated, is called a moving bed.

In fluidized bed reactors, the catalyst-supporting carrier particles are suspended in the reaction fluid and move in the reactor because the reaction fluid operates such that the catalyst layer exhibits the characteristics as if it were a fluid.

In the present disclosure, both a fixed bed reactor and a fluidized bed reactor can be used, and a fixed bed reactor is preferable because it has a wide selection of carrier shapes and can suppress carrier wear. As a fixed bed reactor, there are tubular reactors and vessel type reactors, and a tubular reactor can be preferably used because of the ease of controlling the reaction temperature. Further, a multi-tube heat exchange reaction in which a large number of reaction tubes having a small tube diameter are arranged in parallel and a heat medium is circulated to the outside can be adopted. In a case in which plural reactors are provided in series, plural catalyst layers are provided.

The catalyst layer may have at least one layer, and may have two or more layers.

When the reaction temperature of the catalyst layer lowers, the conversion rate of the raw material decreases. Therefore, it is preferable to maintain the reaction temperature of the catalyst layer at a desired temperature so that a high conversion rate can be maintained. An example for maintaining the reaction temperature of the catalyst layer at a desired temperature includes a method of heating the catalyst layer from the outside with a heat medium or the like.

The specific chlorofluoroolefin and hydrogen usually react at a part of the catalyst layer (hereinafter referred to as "reaction region"). In a case in which the reaction temperature of the catalyst layer is maintained at a desired temperature, the temperature of the upstream side of the reaction region of the catalyst layer is usually maintained by heating. In the present disclosure, the temperature of the upstream side of the reaction region maintained by this heating is referred to as "temperature of the catalyst layer".

From the viewpoint of effectively advancing the reaction, the temperature of the catalyst layer is preferably 30° C. or higher, more preferably 35° C. or higher, and even more preferably 40° C. or higher. Further, from the viewpoint of suppressing by-production of an over-reduced product, 350°

C. or lower is preferable, 300° C. or lower is more preferable, 250° C. or lower is even more preferable, and 200° C. or lower is particularly preferable.

The catalyst usually deteriorates over time as the reaction progresses. The reaction region starts from the introduction portion of the raw material mixed gas at the beginning of the reaction. When the catalyst at the introduction portion of the raw material mixed gas deteriorates with time as the reaction progresses, the reaction region moves to the downstream side in the gas flow direction.

Since the high-temperature generated gas that is generated in the reaction region flows into the vicinity of the downstream side of the reaction region, the vicinity of the downstream side usually has the highest temperature in the catalyst layer. In the present disclosure, the temperature in the region of the catalyst layer having the highest temperature is referred to as "the maximum temperature of the catalyst layer". The temperature further downstream from the vicinity of the downstream side is usually lower than the maximum temperature of the catalyst layer as the distance from the reaction region increases.

An example of a method of measuring the maximum temperature of the catalyst layer includes a measurement method using a plug-in type thermometer. As described above, since the reaction region moves to the downstream side in the gas flow direction over time, the region showing the maximum temperature of the catalyst layer also moves with the movement of the reaction region. Therefore, the measurement portion of the plug-in type thermometer is disposed in advance at the gas introduction portion of the catalyst layer, and after the reaction starts, the measurement portion is moved to the downstream side in the gas flow direction as the reaction progresses, and the maximum temperature of the catalyst layer can be measured.

In the present disclosure, the "gas introduction portion" means a location of the catalyst layer at which the raw material mixed gas is introduced.

Examples of the method of suppressing the maximum temperature of the catalyst layer to a desired temperature include a method of dividing the introduction of hydrogen into the catalyst layer (method ($\alpha$1)). The method ($\alpha$1) tends to maintain high productivity while controlling the maximum temperature of the catalyst layer to a desired temperature or lower.

In the method ($\alpha$1), the number of hydrogen introduction locations is not particularly limited, and may be two locations or three or more locations. Examples of a case in which the number of hydrogen introduction locations is two includes a case of providing a total of two locations in which one location is from the gas introduction portion where hydrogen contained in the raw material mixed gas is introduced, and another location is where only hydrogen gas is introduced (hereinafter referred to as the "hydrogen introduction portion").

From the viewpoint of being able to simplify the process, two locations are preferable. From the viewpoint of being able to disperse the reaction region in the catalyst layer without changing the amount of the specific chlorofluoroolefin introduced, and being able to prevent the generation of reaction heat from being concentrated in one location, such that productivity is not reduced, and being able to suppress local excessive heat generation of the catalyst layer, three or more locations are preferable.

Regarding the division ratio of the hydrogen in a case of dividing the introduction of hydrogen, from the viewpoint of dispersing the reaction region and keeping the maximum temperature of the catalyst layer low, it is preferable to divide the introduction of hydrogen evenly at each location.

Methods of providing the hydrogen introduction portions include a method ($\alpha$1-1) in which a mixed gas of a part of the hydrogen to be introduced into the catalyst layer and a total amount of the specific chlorofluoroolefin is introduced, as the raw material mixed gas, from the gas introduction portion (located at the most upstream side in the gas flow direction) of the catalyst layer, and the remainder of the hydrogen is introduced from one or more hydrogen introduction portions downstream from the gas introduction portion. As a result, hydrogen is further introduced from the hydrogen introduction portions into the gas that has flowed from the upstream (usually, the generated gas after part of the specific chlorofluoroolefin reacts with hydrogen), and the hydrogen reacts with the unreacted specific chlorofluoroolefin at the downstream side from the hydrogen introduction portions. The generated gas in which the specific chlorofluoroolefin and hydrogen are sufficiently reacted is discharged from the gas discharging portion located at the most downstream side in the gas flow direction of the catalyst layer.

In the method ($\alpha$1-1), it is preferable that at least a part of the hydrogen in the raw material mixed gas is reacting with the specific chlorofluoroolefin between the gas introduction portion and the first hydrogen introduction portion. Further, it is preferable that the hydrogen introduction portion at the most downstream side in the gas flow direction is provided at a position at which the hydrogen introduced from the hydrogen introduction portion at the most downstream side and the unreacted specific chlorofluoroolefin can be sufficiently reacted between the hydrogen introduction portion at the most downstream side and the gas discharging portion of the catalyst layer.

When two or more catalyst layers are continuously provided in the reactor, methods of introducing hydrogen include, for example, a method of introducing part of the hydrogen together with the specific chlorofluoroolefin from the gas introduction portion of the first catalyst layer, and introducing the remainder of the hydrogen from a hydrogen filling portion of the catalyst layer in the second and subsequent catalyst layers.

Examples of the method of suppressing the maximum temperature of the catalyst layer to a desired temperature other than the method ($\alpha$1) include a method of flowing an inert gas through the catalyst layer together with the specific chlorofluoroolefin and hydrogen (method ($\alpha$2)). By flowing the inert gas and adjusting the concentrations of the specific chlorofluoroolefin and hydrogen flowing in the catalyst layer, it is possible to suppress an excessive temperature rise of the catalyst layer due to reaction heat. Further, a dilution gas other than the inert gas can be used instead of the inert gas or together with the inert gas.

Examples of the inert gas include nitrogen gas, noble gas, and fluorocarbons that are inert to a hydrogenation reaction. Examples of the dilution gas other than the inert gas include hydrogen chloride.

From the viewpoint of easily keeping the maximum temperature of the catalyst layer low, easily suppressing by-production of an over-reduced product, and easily suppressing deterioration of the catalyst, the amount of the inert gas introduced to the catalyst layer is, with respect to 1 mol of the specific chlorofluoroolefin, preferably 0.1 mol or more, and more preferably 0.5 mols of more. Further, from the viewpoint of collection rate of the inert gas, the amount of the inert gas that is introduced is, with respect to 1 mol of the specific chlorofluoroolefin, preferably 10 mol or less, and more preferably 4 mol or less.

Methods of suppressing the maximum temperature of the catalyst layer to a desired temperature other than the method (α1) and the method (α2) include a method (method (α3)) of setting a heat medium temperature for heating the reactor to a lower temperature, with the dew point of the raw material mixed gas as the lower limit. By keeping the temperature of the heat medium low, it is possible to remove the reaction heat more quickly, and it is possible to suppress an excessive temperature rise of the catalyst layer.

In the method (α3), the lower the temperature of the catalyst layer is, the more advantageous it is in terms of suppressing by-production of an over-reduced product which is difficult to separate from the specific hydrofluoroolefin.

As the method of suppressing the maximum temperature of the catalyst layer to a desired temperature, it is preferable to use the method (α1), the method (α2) or the method (α3), or two or three of these methods in combination.

From the viewpoint of handleability, the reaction pressure is preferably normal pressure.

The contact time of the specific chlorofluoroolefin gas with the catalyst is preferably 0.5 seconds to 60 seconds, and more preferably 1 second to 40 seconds. This contact time is the contact time of the specific chlorofluoroolefin gas calculated from the amount of gas introduced into the reactor and the volume of the catalyst layer.

From the viewpoint of easily suppressing by-production of an over-reduced product, the ratio of the specific chlorofluoroolefin to hydrogen which are introduced into the catalyst layer, as a ratio of the total number of moles of hydrogen to the number of moles of chlorine atoms in the specific chlorofluoroolefin ($H_2/Cl$), is preferably 0.7 or less, more preferably 0.6 or less, and even more preferably 0.5 or less. Further, from the view point of the yield of the reaction product, the ratio ($H_2/Cl$) is preferably 0.1 or more, and more preferably 0.2 or more.

In the method (α), in the catalyst layer, the linear velocity u of the specific chlorofluoroolefin gas represented by the following Formula (H) is preferably 0.1 cm/sec to 100 cm/sec, and more preferably 1 cm/sec to 30 cm/sec. This linear velocity u is the linear velocity of the specific chlorofluoroolefin gas calculated from the amount of gas introduced into the reactor and the volume of the catalyst layer. If the linear velocity u of the specific chlorofluoroolefin gas is 0.1 cm/sec or more, productivity improves. If the linear velocity u of the specific chlorofluoroolefin gas is 100 cm/sec or less, the conversion rate of the chlorofluoroolefin and hydrogen improves.

$$u = (W/100) \times V/S \quad (H)$$

In Formula (H), W indicates the concentration (mol %) of the specific chlorofluoroolefin gas in the total gas flowing through the catalyst layer, V indicates the flow rate (cm$^3$/sec) of the total gas flowing through the catalyst layer, and S indicates the cross-sectional area (cm$^2$) of the catalyst layer with respect to the gas flow direction.

Examples of the reactor used in the method (α) include known reactors into which a catalyst can be filled and a catalyst layer can be formed.

Examples of the material of the reactor include glass; iron, nickel, and alloys containing these as main components, and the like.

The generated gas after the reaction contains unreacted raw materials, intermediate products, and hydrogen chloride in addition to the target specific hydrofluoroolefin.

Hydrogen chloride contained in the generated gas can be removed by blowing the generated gas into an alkaline aqueous solution to neutralize it. Examples of the alkali used in the alkaline aqueous solution include sodium hydroxide and potassium hydroxide.

As a method of separating the specific hydrofluoroolefin and the unreacted specific chlorofluoroolefin from the generated gas, for example, a known method such as distillation can be adopted.

The chlorofluoroolefin that is separated from the generated gas after the reaction can be reused. For example, the separated HCFO-1224yd may be reacted with hydrogen as a specific chlorofluoroolefin together with CFO-1214ya, or only the HCFO-1224yd may be reacted with hydrogen, separate from CFO-1214ya.

In a case in which a mixture of CFO-1214ya and HCFO-1224yd are used as the specific chlorofluoroolefin, since HCFO-1224yd is an intermediate product when obtaining HFO-1234yf from the CFO-1214ya, a mixture having a low ratio of HCFO-1224yd is usually used. Therefore, the ratio of HCFO-1224yd with respect to the total amount of CFO-1214ya and HCFO-1224yd is preferably 50 mol % or less, and more preferably 25 mol % or less.

<Method (β)>

In the method (β), it is preferable to use a medium. Examples of the medium include water, an organic solvent such as alcohol, and the like.

The amount of the medium used is preferably 10 parts by mass to 100 parts by mass with respect to 100 parts by mass of the specific chlorofluoroolefin.

Methods of supplying hydrogen include a method of blowing hydrogen gas into a liquid containing the catalyst-supporting carrier, the specific chlorofluoroolefin, and a medium to be used as necessary, and a method in which a medium in which hydrogen is dissolved in advance by pressurization is added to a liquid containing a catalyst-supporting carrier and a specific chlorofluoroolefin.

The reaction between the specific chlorofluoroolefin and hydrogen in the method (13) may be a batch type or a continuous type.

The reaction temperature in the method (β) is preferably 0° C. to 200° C. If the reaction temperature is 0° C. or higher, the conversion rate of the specific chlorofluoroolefin and hydrogen improves. If the reaction temperature is 200° C. or lower, it is easy to suppress by-production of an over-reduced product.

As the reaction pressure in the method (β), a gauge pressure is preferrably 0.01 MPaG to 5 MPaG, and more preferably 0.1 MPaG to 1 MPaG.

The reaction time in the method (β) is preferably 1 hour to 50 hours in the case of a batch type, and preferably 1 second to 60 seconds in the case of a continuous type.

From the viewpoint of easily suppressing by-production of an over-reduced product, the amount of hydrogen that is supplied in the method (β), as a ratio of the number of moles of supplied hydrogen to the number of moles of chlorine atoms in the specific chlorofluoroolefin ($H_2/Cl$), is preferably 0.7 or less, more preferably 0.6 or less, and even more preferably 0.5 or less. Further, from the viewpoint of the yield of the reaction product, the ratio ($H_2/Cl$) is preferably 0.1 or more, and more preferably 0.2 or more. The amount of hydrogen supplied means the amount of hydrogen dissolved in the reaction solution.

The reaction solution after the reaction contains unreacted raw materials, intermediate products, and hydrogen chloride in addition to the target specific hydrofluoroolefin. Hydrogen chloride contained in the reaction solution can be removed by adding an alkali to the reaction solution to neutralize it. Examples of the alkali include sodium hydroxide, potassium hydroxide and the like.

The alkali may be added in advance to the reaction solution used for the reaction.

As a method of separating the specific hydrofluoroolefin and the unreacted specific chlorofluoroolefin from the reaction solution, for example, a known method such as distillation can be adopted.

The specific chlorofluoroolefin that is separated from the reaction solution can be reused. For example, the separated HCFO-1224yd may be reacted with hydrogen as a specific chlorofluoroolefin of the raw material together with CFO-1214ya, or the HCFO-1224yd may separated from CFO-1214ya and only the HCFO-1224yd reacted with hydrogen.

Examples of the reactor used in the method (β) include known reactors capable of bringing reaction raw materials into contact with each other in the presence of a catalyst to cause a liquid phase reaction.

Examples of the material of the reactor include glass; iron, nickel, and alloys containing these as main components, and the like.

EXAMPLES

Hereinafter, the present disclosure will be described in detail with reference to Examples and Comparative Examples. However, the present disclosure is not limited to the following examples.

Comparative Example 1

[Preparation of Palladium-Supporting Silica]

Palladium-supporting silica was prepared by the impregnation method. Explaining the specific preparation method, a palladium nitrate aqueous solution was added to a silica gel as a carrier (Fuji Silysia Chemical Ltd., CARiACT G-6 (specific surface area: 470 m$^2$/g, particle size: 75 μm to 250 μm, purity>99%)) such that the amount of palladium supported was 3 parts by mass with respect to 100 parts by mass of the palladium-supporting silica, and the dispersion was stirred for 5 minutes, thereby preparing a silica gel dispersion. After stirring, the silica gel dispersion was allowed to stand for 24 hours. Thereafter, the silica gel was dried at 110° C., calcined at 130° C. for 1 hour, and subsequently calcined at 400° C. for 1 hour. Next, a reduction treatment was carried out on a part of the sample by leaving it at 400° C. for 1 hour with a flow of hydrogen ($H_2$) gas at normal pressure. Immediately after the reduction was completed, the flowing gas was switched to argon (Ar) gas and the sample was allowed to cool to room temperature, and palladium-supporting silica (Pd/SiO$_2$) was obtained.

Example 1

[Preparation of Pd$_3$Bi-Supporting Silica 1]

Pd$_3$Bi-supporting silica 1 was prepared by the co-impregnation method. Explaining the specific preparation method, a nitric acid solution of palladium nitrate and bismuth nitrate pentahydrate, containing palladium and bismuth at an atom ratio of 3/1, was added to a silica gel as a carrier (Fuji Silysia Chemical Ltd., CARiACT G-6) such that the amount of palladium supported was 3 parts by mass with respect to 100 parts by mass of the Pd$_3$Bi-supporting silica 1, and the dispersion was stirred for 5 minutes, thereby preparing a silica gel dispersion. After stirring, the silica gel dispersion was allowed to stand for 24 hours. Thereafter, the silica gel was dried at 110° C., and next, a reduction treatment was carried out by leaving the silica gel at 800° C. for 1 hour with a flow of H$_2$ gas at normal pressure. Immediately after the reduction was completed, the flowing gas was switched to Ar gas and the the silica gel was allowed to cool to room temperature, and Pd$_3$Bi-supporting silica 1 (Pd$_3$Bi/SiO$_2$ (1)) was obtained.

Reference Example 1

[Preparation of Pd$_3$Bi-Supporting Silica 2]

Pd$_3$Bi-supporting silica 2 was prepared by the successive impregnation method. Explaining the specific preparation method, a nitric acid solution in which bismuth nitrate pentahydrate was dissolved was added to the palladium-supporting silica prepared by the above-described method such that the amount of palladium and bismuth supported was 3/1 in terms of atom ratio, and the dispersion was stirred for 5 minutes, thereby preparing a palladium-supporting silica dispersion. After stirring, the palladium-supporting silica dispersion was allowed to stand for 24 hours. Thereafter, the palladium-supporting silica was dried at 110° C., and next, a reduction treatment was carried out by leaving the palladium-supporting silica at 800° C. for 1 hour with a flow of H$_2$ gas at normal pressure. Immediately after the reduction was completed, the flowing gas was switched to Ar gas and the palladium-supporting silica was allowed to cool to room temperature, and Pd$_3$Bi-supporting silica 2 (Pd$_3$Bi/SiO$_2$ (2)) was obtained.

Example 2

[Preparation of Pd$_3$In-Supporting Silica]

Pd$_3$In-supporting silica was prepared by the successive impregnation method. Explaining the specific preparation method, an aqueous solution in which indium nitrate n-hydrate was dissolved was added to the palladium-supporting silica prepared by the above-described method such that the amount of palladium and indium supported was 3/1 in terms of atom ratio, and the dispersion was stirred for 5 minutes, thereby preparing a palladium-supporting silica dispersion. After stirring, the palladium-supporting silica dispersion was allowed to stand for 24 hours. Thereafter, the palladium-supporting silica was dried at 110° C., and next, a reduction treatment was carried out by leaving the palladium-supporting silica at 800° C. for 1 hour with a flow of H$_2$ gas at normal pressure. Immediately after the reduction was completed, the flowing gas was switched to Ar gas and the palladium-supporting silica was allowed to cool to room temperature, and Pd$_3$In-supporting silica (Pd$_3$In/SiO$_2$) was obtained.

Example 3

[Preparation of Pd$_3$Sn-Supporting Silica]

Pd$_3$Sn-supporting silica was prepared by the successive impregnation method. Explaining the specific preparation method, an ethanol solution in which stannous chloride dihydrate was dissolved was added to the palladium-supporting silica prepared by the above-described method such that the amount of palladium and tin supported was 3/1 in terms of atom ratio, and the dispersion was stirred for 5 minutes, thereby preparing a palladium-supporting silica dispersion. After stirring, the palladium-supporting silica dispersion was allowed to stand for 24 hours. Thereafter, the palladium-supporting silica was dried at 110° C., and next, a reduction treatment was carried out by leaving the palladium-supporting silica at 800° C. for 1 hour with a flow of $H_2$ gas at normal pressure. Immediately after the reduction was completed, the flowing gas was switched to Ar gas and the palladium-supporting silica was allowed to cool to room temperature, and $Pd_3Sn$-supporting silica ($Pd_3Sn/SiO_2$) was obtained.

Example 4

[Preparation of $Pd_3Pb$-Supporting Silica]

$Pd_3Pb$-supporting silica was prepared by the successive impregnation method. Explaining the specific preparation method, an aqueous solution in which lead nitrate was dissolved was added to the palladium-supporting silica prepared by the above-described method such that the amount of palladium and lead supported was 3/1 in terms of atom ratio, and the dispersion was stirred for 5 minutes, thereby preparing a palladium-supporting silica dispersion. After stirring, the palladium-supporting silica dispersion was allowed to stand for 24 hours. Thereafter, the palladium-supporting silica was dried at 110° C., and next, a reduction treatment was carried out by leaving the palladium-supporting silica at 800° C. for 1 hour with a flow of $H_2$ gas at normal pressure. Immediately after the reduction was completed, the flowing gas was switched to Ar gas and the palladium-supporting silica was allowed to cool to room temperature, and $Pd_3Pb$-supporting silica ($Pd_3Pb/SiO_2$) was obtained.

Comparative Examples 2 to 5

[Preparation of Pd—Bi Solid Solution Alloy-Supporting Silicas 1 to 4]

Pd—Bi solid solution alloy-supporting silicas 1 to 4 were prepared by the co-impregnation method. Explaining the specific preparation method, except for changing the reduction treatment conditions with a flow of $H_2$ gas at normal pressure to 400° C. for 1 hour (Pd—Bi solid solution alloy-supporting silica 1 (Comparative Example 2)), 500° C. for 1 hour (Pd—Bi solid solution alloy-supporting silica 2 (Comparative Example 3)), 600° C. for 1 hour (Pd—Bi solid solution alloy-supporting silica 3 (Comparative Example 4)), and 700° C. for 1 hour (Pd—Bi solid solution alloy-supporting silica 4 (Comparative Example 5)) the method was the same as in the case of preparing $Pd_3Bi$-supporting silica 1, and Pd—Bi solid solution alloy-supporting silicas 1 to 4 (Pd—Bi/$SiO_2$ (1) to (4)) were obtained.

Comparative Example 6

[Preparation of Pd—Pb Solid Solution Alloy-Supporting Silica]

Pd—Pb solid solution alloy-supporting silica was prepared by the successive impregnation method. Explaining the specific preparation method, an aqueous solution in which lead nitrate was dissolved was added to the palladium-supporting silica prepared by the above-described method such that the amount of palladium and lead supported was 3/1 in terms of atom ratio, and the dispersion was stirred for 5 minutes, thereby preparing a palladium-supporting silica dispersion. After stirring, the palladium-supporting silica dispersion was allowed to stand for 24 hours. Thereafter, the palladium-supporting silica was dried at 110° C., and next, a reduction treatment was carried out by leaving the palladium-supporting silica at 600° C. for 1 hour with a flow of $H_2$ gas at normal pressure. Immediately after the reduction was completed, the flowing gas was switched to Ar gas and the palladium-supporting silica was allowed to cool to room temperature, and Pd—Pb solid solution alloy-supporting silica (Pd—Pb/$SiO_2$) was obtained.

[XRD Measurement]

It was confirmed by XRD whether or not the catalyst supported on the catalyst-supporting carrier was an intermetallic compound. The measurement was performed using Rigaku Corporation's SmartLab according to the measurement procedure of normal powder X-ray diffraction, and CuKα radiation (wavelength: 1.54 Å) was used. The measurement was performed under the following conditions.

Output: 45 kV, 200 mA
Scanning speed: 0.3 deg/min
Step angle: 0.01 deg
Measurement range (2θ): 20 deg to 60 deg The XRD analysis results of each catalyst were as follows.

[Analysis Results (Pd/$SiO_2$)]

The X-ray diffraction angle (2θ) of the (111) plane of Pd/$SiO_2$ was 40.0 deg.

[Analysis Results ($Pd_3Bi/SiO_2$)]

The X-ray diffraction angle (2θ) of the (221) plane of $Pd_3Bi/SiO_2$ (1) was 40.8 deg. The catalyst supported on the $SiO_2$ was a specific intermetallic compound containing $Pd_3Bi$.

The X-ray diffraction angle (2θ) of the (221) plane of $Pd_3Bi/SiO_2$ (2) was 40.8 deg. The catalyst supported on the $SiO_2$ was a specific intermetallic compound containing $Pd_3Bi$.

[Analysis Results ($Pd_3In/SiO_2$)]

The X-ray diffraction angle (2θ) of the (112) plane of $Pd_3In/SiO_2$ was 39.2 deg. The catalyst supported on the $SiO_2$ was a specific intermetallic compound containing $Pd_3In$.

[Analysis Results ($Pd_3Sn/SiO_2$)]

The X-ray diffraction angle (2θ) of the (004) plane of $Pd_3Sn/SiO_2$ was 39.3 deg. The catalyst supported on the $SiO_2$ was a specific intermetallic compound containing $Pd_3Sn$.

[Analysis Results ($Pd_3Pb/SiO_2$)]

The X-ray diffraction angle (2θ) of the (111) plane of $Pd_3Pb/SiO_2$ was 38.6 deg. The catalyst supported on the $SiO_2$ was a specific intermetallic compound containing $Pd_3Pb$.

[Analysis Results (Pd—Bi/$SiO_2$)]

The X-ray diffraction angle (2θ) of the (111) plane of Pd—Bi/$SiO_2$ (1) obtained by hydrogen reduction at 400° C. was 39.3 deg. The catalyst supported on the $SiO_2$ was not a specific intermetallic compound.

The X-ray diffraction angle (2θ) of the (111) plane of Pd—Bi/$SiO_2$ (2) obtained by hydrogen reduction at 500° C. was 39.1 deg. The catalyst supported on the $SiO_2$ was not a specific intermetallic compound.

The X-ray diffraction angle (2θ) of the (111) plane of Pd—Bi/$SiO_2$ (3) obtained by hydrogen reduction at 600° C. was 38.6 deg. The catalyst supported on the $SiO_2$ was not a specific intermetallic compound.

The X-ray diffraction angle (2θ) of the (111) plane of Pd—Bi/$SiO_2$ (4) obtained by hydrogen reduction at 700° C. was 38.5 deg. The catalyst supported on the $SiO_2$ was not a specific intermetallic compound.

[Analysis Results (Pd—Pb/SiO$_2$)]

The X-ray diffraction angle (2θ) of the (111) plane of Pd—Pb/SiO$_2$ was 38.7 deg. The catalyst supported on the SiO$_2$ was not a specific intermetallic compound.

[Reaction Evaluation]

(Reactor)

As a reactor, a U-shaped reaction tube made of stainless steel (SUS316) and having an inner diameter of 7.53 mm was prepared. The reaction tube was filled with a SUS316 straight tube and silica wool in order to support the catalyst bed. In order to control the temperature, a reactor in which a thermocouple was fixed to the immediate side of the electric furnace installed around the reaction tube was used.

(Reaction conditions in a case in which Pd/SiO$_2$ was used)

0.015 g of Pd/SiO$_2$ was filled into the location at which the aforementioned silica wool of the reaction tube was filled in, and the reaction was carried out. First, reduction pretreatment was carried out by leaving the Pd/SiO$_2$ at 400° C. for 1 hour with a flow of H$_2$ gas at normal pressure (40 mL/min). After the pretreatment was completed, the flow of gas was switched to 25 mL/min of Ar gas and the Pd/SiO$_2$ was allowed to cool.

Thereafter, the reactor was heated to 90° C. by an electric furnace, and a raw material mixed gas consisting of CFO-1214ya, Ar, and H$_2$ was introduced into the reactor. Regarding the introduction of raw materials, a mixed gas of Ar and H$_2$ was bubbled into the raw materials cooled in an ice bath, and the obtained raw material mixed gas was introduced into the reactor. The reaction was carried out under atmospheric pressure and the following conditions.

Reaction gas composition (volume ratio): CFO-1214ya:H$_2$:Ar=1.0:1.0:3.4

Total reaction gas flow rate: 39 mL/min (Reaction Conditions in a Case in which Pd$_3$Bi/SiO$_2$ was Used)

0.15 g of Pd$_3$Bi/SiO$_2$ (1) was filled into the location at which the aforementioned silica wool of the reaction tube was filled in, and the reaction was carried out. First, reduction pretreatment was carried out by leaving the Pd$_3$Bi/SiO$_2$ (1) at 400° C. for 1 hour with a flow of H$_2$ gas at normal pressure (40 mL/min). After the pretreatment was completed, the flow of gas was switched to 25 mL/min of Ar gas and the Pd$_3$Bi/SiO$_2$ (1) was allowed to cool.

Thereafter, the reactor was heated to 150° C. by an electric furnace, and a raw material mixed gas consisting of CFO-1214ya, Ar, and H$_2$ was introduced into the reactor. Regarding the introduction of raw materials, a mixed gas of Ar and H$_2$ was bubbled into the raw materials cooled in an ice bath, and the obtained raw material mixed gas was introduced into the reactor. The reaction was carried out under atmospheric pressure and the following conditions.

Reaction gas composition (volume ratio): CFO-1214ya:H$_2$:Ar=1.0:1.0:3.4

Total reaction gas flow rate: 39 mL/min (Reaction Conditions in a Case in which Pd$_3$In/SiO$_2$ was Used)

0.15 g of Pd$_3$In/SiO$_2$ was filled into the location at which the aforementioned silica wool of the reaction tube was filled in, and the reaction was carried out. First, reduction pretreatment was carried out by leaving the Pd$_3$In/SiO$_2$ at 400° C. for 1 hour with a flow of H$_2$ gas at normal pressure (40 mL/min). After the pretreatment was completed, the flow of gas was switched to 25 mL/min of Ar gas and the Pd$_3$In/SiO$_2$ was allowed to cool.

Thereafter, the reactor was heated to 90° C. by an electric furnace, and a raw material mixed gas consisting of CFO-1214ya, Ar, and H$_2$ was introduced into the reactor. Regarding the introduction of raw materials, a mixed gas of Ar and H$_2$ was bubbled into the raw materials cooled in an ice bath, and the obtained raw material mixed gas was introduced into the reactor. The reaction was carried out under atmospheric pressure and the following conditions.

Reaction gas composition (volume ratio): CFO-1214ya:H$_2$:Ar=1.0:1.0:3.4

Total reaction gas flow rate: 39 mL/min (Reaction Conditions in a Case in which Pd$_3$Sn/SiO$_2$ was Used)

0.3 g of Pd$_3$Sn/SiO$_2$ was filled into the location at which the aforementioned silica wool of the reaction tube was filled in, and the reaction was carried out. First, reduction pretreatment was carried out by leaving the Pd$_3$Sn/SiO$_2$ at 400° C. for 1 hour with a flow of H$_2$ gas at normal pressure (40 mL/min). After the pretreatment was completed, the flow of gas was switched to 25 mL/min of Ar gas and the Pd$_3$Sn/SiO$_2$ was allowed to cool.

Thereafter, the reactor was heated to 150° C. by an electric furnace, and a raw material mixed gas consisting of CFO-1214ya, Ar, and H$_2$ was introduced into the reactor. Regarding the introduction of raw materials, a mixed gas of Ar and H$_2$ was bubbled into the raw materials cooled in an ice bath, and the obtained raw material mixed gas was introduced into the reactor. The reaction was carried out under atmospheric pressure and the following conditions.

Reaction gas composition (volume ratio): CFO-1214ya:H$_2$:Ar=1.0:1.0:3.4

Total reaction gas flow rate: 39 mL/min (Reaction Conditions in a Case in which Pd$_3$Pb/SiO$_2$ was Used)

0.3 g of Pd$_3$Pb/SiO$_2$ was filled into the location at which the aforementioned silica wool of the reaction tube was filled in, and the reaction was carried out. First, reduction pretreatment was carried out by leaving the Pd$_3$Pb/SiO$_2$ at 400° C. for 1 hour with a flow of H$_2$ gas at normal pressure (40 mL/min). After the pretreatment was completed, the flow of gas was switched to 25 mL/min of Ar gas and the Pd$_3$Pb/SiO$_2$ was allowed to cool.

Thereafter, the reactor was heated to 150° C. by an electric furnace, and a raw material mixed gas consisting of CFO-1214ya, Ar, and H$_2$ was introduced into the reactor. Regarding the introduction of raw materials, a mixed gas of Ar and H$_2$ was bubbled into the raw materials cooled in an ice bath, and the obtained raw material mixed gas was introduced into the reactor. The reaction was carried out under atmospheric pressure and the following conditions.

Reaction gas composition (volume ratio): CFO-1214ya:H$_2$:Ar=1.0:1.0:3.4

Total reaction gas flow rate: 39 mL/min (Reaction Conditions in a Case in which Pd—Bi/SiO$_2$ was Used)

0.050 g of Pd—Bi/SiO$_2$ was filled into the location at which the aforementioned silica wool of the reaction tube was filled in, and the reaction was carried out. The subsequent reaction procedure was the same as described above in (Reaction conditions in a case in which Pd$_3$Bi/SiO$_2$ was used).

(Reaction Conditions in a Case in which Pd—Pb/SiO$_2$ was Used)

0.050 g of Pd—Pb/SiO$_2$ was filled into the location at which the aforementioned silica wool of the reaction tube was filled in, and the reaction was carried out. The subsequent reaction procedure was the same as described above in (Reaction conditions in a case in which Pd$_3$Bi/SiO$_2$ was used).

(Gas Analysis Conditions)

Analysis of the product by gas phase reaction was performed using GC-14B manufactured by Shimadzu Corporation. Regarding columns, two Agilent Technologies DB-1301 (60 m×0.25 mm, d.f.=1.00 μm) were connected and used.

The gas that had passed through the reactor was passed through two consecutive traps and collected with a syringe. Teflon (registered trademark) containers into which 40 mL of a 1 mol/L NaOH aqueous solution had been put into were used as the traps at 25° C. Analysis of the composition was performed using a gas chromatograph, and the selectivity of HFO-1234yf was determined from the area of the peaks as the analysis result by the following Formula.

(Calculation of HFO-1234yf Selectivity)

The selectivity of HFO-1234yf was calculated from the following Formula.

Selectivity of $HFO\text{-}1234yf = 100 \times A_{1234yf}/(\Sigma A_i - A_x - A_{ya})$ (%)

$\Sigma A_i$: Total area of all peaks in the composition results of the generated gas $A_x$: Area of impurities originally contained in CFO-1214ya $A_{ya}$: Area of CFO-1214ya $A_{1234yf}$: Area of HFO-1234yf For each area, the peak area, which is the analysis result of the gas chromatograph, was used.

(Calculation of Valuable Material Selectivity)

Valuable material selectivity=($HFO\text{-}1234yf$ selectivity)+($HCFO\text{-}1224yd$ selectivity)

$HCFO\text{-}1224yd$ selectivity=$100 \times A_{1224yd}/(\Sigma A_i - A_x - A_{ya})$ (%)

$A_{1224yd}$: area of HCFO-1224yd

For the area of HCFO-1224yd, the peak area, which is the analysis result of the gas chromatography, was used.

(Calculation of Valuable Material Yield)

Valuable material yield=(valuable material selectivity×$CFO\text{-}1214ya$ conversion rate)/100(%)

$CFO\text{-}1214ya$ conversion rate=$100 - ((100 \times A_{ya})/(\Sigma A_i - A_x))$ (%)

Definition of valuable material: Since the intermediate product can be converted into the target product by collecting and re-reacting (it is difficult to convert an over-reduced product to the target product), the target reaction product and the intermediate product were regarded as valuable materials.

(Analysis Results)

When the reaction between CFO-1214ya and hydrogen was carried out, the CFO-1214ya conversion rate, the HCFO-1224yd selectivity, the HFO-1234yf selectivity, the valuable material selectivity, and the valuable material yield were determined as described above. The results are shown in Table 1 below.

TABLE I

| | Catalyst | 1214ya Conversion rate [%] | 1224yd Selectivity [A] | 1234yf Selectivity [A] | Valuable Material Selectivity [%] | Valuable Material Yield [Vo] |
|---|---|---|---|---|---|---|
| Example 1 | Pd$_3$Bi | 54.1 | 22.9 | 70.7 | 93.7 | 50.7 |
| Example 2 | Pd$_3$In | 59.8 | 9.4 | 72.6 | 82.0 | 49.0 |
| Example 3 | Pd$_3$Sn | 59.0 | 9.0 | 74.5 | 83.5 | 49.3 |
| Example 4 | Pd$_3$Pb | 64.8 | 12.2 | 78.3 | 90.5 | 58.6 |
| Comparative Example 1 | Pd | 55.9 | 8.1 | 56.7 | 64.8 | 36.2 |
| Comparative Example 2 | Pd—Bi | 43.3 | 22.4 | 67.4 | 89.8 | 38.9 |
| Comparative Example 3 | | 42.1 | 21.1 | 68.8 | 89.9 | 37.8 |
| Comparative Example 4 | | 35.6 | 16.6 | 71.0 | 87.6 | 31.2 |
| Comparative Example 5 | | 38.7 | 17.1 | 71.3 | 88.4 | 34.2 |
| Comparative Example 6 | Pd—Pb | 66.0 | 9.6 | 58.7 | 68.3 | 45.1 |

As can be seen from Table 1, it was found that the selectivity of HFO-1234yf can be improved by using an intermetallic compound catalyst that has bismuth as the second element and that is supported on a carrier. Further, it was found that the valuable material selectivity and the valuable material yield containing HCFO-1224yd were also favorable.

Furthermore, it was found that the selectivity of HFO-1234yf can be improved by using an intermetallic compound catalyst that has indium, tin or lead as the second element and that is supported on the carrier. Further, it was found that the valuable material selectivity and the valuable material yield containing HCFO-1224yd were also favorable.

The invention claimed is:

1. A method of producing a hydrofluoroolefin, comprising:

reacting a chlorofluoroolefin that is represented by following Formula (I) or following Formula (II) and that has 8 or less carbon atoms with a hydrogen molecule, in the presence of an intermetallic compound containing at least one first metal that is selected from the group consisting of palladium, platinum, rhodium, copper and iridium, and containing a second metal that is different from the first metal, to obtain a hydrofluoroolefin in which a hydrogen atom is substituted for at least a chlorine atom represented by Cl among chlorine atoms contained in Formula (I) or Formula (II):

(I)

wherein, in Formula (I), each of $R^1$ to $R^3$ independently represents a hydrogen atom, a fluorine atom, a chlorine atom or an alkyl group that may be substituted with a fluorine atom or a chlorine atom, and at least one fluorine atom is included in Formula (I);

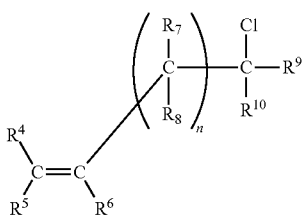
(II)

wherein, in Formula (II), each of $R^4$ to $R^{10}$ independently represents a hydrogen atom, a fluorine atom, a chlorine atom or an alkyl group that may be substituted with a fluorine atom or a chlorine atom, at least one fluorine atom is included in Formula (II), and n is an integer from 0 to 5.

2. The method of producing a hydrofluoroolefin according to claim 1, wherein a molar ratio of the first metal to the second metal which are contained in the intermetallic compound, first metal/second metal, is from 1 to 5.

3. The method of producing a hydrofluoroolefin according to claim 2, wherein the molar ratio of the first metal to the second metal which are contained in the intermetallic compound, first metal/second metal, is from 2 to 4.

4. The method of producing a hydrofluoroolefin according to claim 1, wherein the intermetallic compound is at least one selected from the group consisting of $Pd_3Bi$, $Pd_3In$, $Pd_3Sn$ and $Pd_3Pb$.

5. The method of producing a hydrofluoroolefin according to claim 1, wherein the chlorofluoroolefin is a compound represented by following Formula (III):

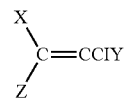
(III)

wherein, in Formula (III), X represents a fluorine atom or a chlorine atom, Y represents a hydrogen atom, a fluorine atom or a chlorine atom, and Z represents a fluorine atom or a methyl group that may be substituted with a fluorine atom.

6. The method of producing a hydrofluoroolefin according to claim 5, wherein the compound represented by Formula (III) includes 1,1-dichloro-2,3,3,3-tetrafluoropropene or 1-chloro-2,3,3,3-tetrafluoropropene.

7. The method of producing a hydrofluoroolefin according to claim 1, wherein the intermetallic compound is supported on a carrier.

8. The method of producing a hydrofluoroolefin according to claim 7, wherein the carrier includes at least one of a carbon material or an oxide material.

9. The method of producing a hydrofluoroolefin according to claim 7, wherein an amount of the intermetallic compound that is supported is from 0.1% by mass to 10% by mass with respect to the carrier.

10. The method of producing a hydrofluoroolefin according to claim 7, wherein the chlorofluoroolefin and the hydrogen molecule are introduced into a catalyst layer that is filled with the carrier supporting the intermetallic compound and are reacted in a gas phase.

11. The method of producing a hydrofluoroolefin according to claim 7, wherein the chlorofluoroolefin and the hydrogen molecule are reacted in a liquid phase in the presence of the carrier that is supporting the intermetallic compound.

\* \* \* \* \*